United States Patent
Venugopala et al.

(10) Patent No.: US 11,974,991 B1
(45) Date of Patent: May 7, 2024

(54) ADENOSINE RECEPTOR ACTIVITY OF METHYL/ETHYL 3-(SUBSTITUTED BENZOYL)-6,8-DIMETHYLINDOLIZINE-2-SUBSTITUTED-1-CARBOXYLATES

(71) Applicant: KING FAISAL UNIVERSITY, Al-Ahsa (SA)

(72) Inventors: Katharigatta N. Venugopala, Al-Ahsa (SA); Buccioni Michela, Camerino (IT); Gabriella Marucci, Cmaerino (IT); Pran Kishore Deb, Ranchi (IN); Mohamed A. Morsy, Al-Ahsa (SA); Bandar Aldhubiab, Al-Ahsa (SA); Mahesh Attimarad, Al-Ahsa (SA); Anroop B. Nair, Al-Ahsa (SA); Nagaraja Sreeharsha, Al-Ahsa (SA); Sandeep Chandrashekharappa, Lucknow (IN); Sheena Shashikanth, Mysore (IN)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/230,585

(22) Filed: Aug. 4, 2023

(51) Int. Cl.
*A61K 31/437* (2006.01)

(52) U.S. Cl.
CPC ................ *A61K 31/437* (2013.01)

(58) Field of Classification Search
CPC ........ A61K 31/437; A61P 35/00; A61P 25/00; A61P 29/00; A61P 37/08; A61P 27/06
USPC ......................................... 514/299
See application file for complete search history.

(56) References Cited

U.S. PATENT DOCUMENTS 11,530,217 B1 * 12/2022 Venugopala ............ A61P 31/06

FOREIGN PATENT DOCUMENTS

CN 113993846 A 1/2022

OTHER PUBLICATIONS

Ghinet et al.: Studies on Indolizines. Evaluation of their biological properties as microtubule-interacting agents and as melanoma targeting compounds. Eur. J. Medicinal Chem., vol. 89, pp. 115-127, 2015.*

Lucescu et al.: Synthesis and biological evaluation of some new indolizine derivatives as antitumoral agents. Lett. in Drug Design and Disc., vol. 13, pp. 479-488,2016.*

Chandrashekharappa, S. et al., "Qualitative anti-tubercular activity of synthetic ethyl 7-acetyl2-substituted-3-(4-substituted benzoyl) indolizine-1-carboxylate analogues", Journal of Applied Pharmaceutical Science vol. 9(02), pp. 124-128, Feb. 2019.

* cited by examiner

*Primary Examiner* — Charanjit Aulakh
(74) *Attorney, Agent, or Firm* — Nath, Goldberg & Meyer; Richard C. Litman

(57) ABSTRACT

Adenosine receptor active compounds including 1,2,3,6,8-pentasubstituted indolizines and methods of using the same for inhibiting adenosine receptor activity are provided. These methods can be used to treat one or more pathological conditions of the central and peripheral nervous systems, such as but not limited to allergies, inflammation, glaucoma, brain ischemia, renal fibrosis, cancer, rheumatoid arthritis, psoriasis fatty liver diseases, stroke, pain, and any combination thereof.

7 Claims, No Drawings

ADENOSINE RECEPTOR ACTIVITY OF METHYL/ETHYL 3-(SUBSTITUTED BENZOYL)-6,8-DIMETHYLINDOLIZINE-2-SUBSTITUTED-1-CARBOXYLATES

BACKGROUND

1. Field

The present disclosure relates to the use of various compounds having adenosine receptor activity and, particularly, to the use of 1,2,3,6,8-pentasubstituted indolizines as adenosine receptor modulators for numerous therapeutic applications.

2. Description of the Related Art

There have been many recent efforts to develop new potent and selective $A_3AR$ (the $A_3$ Adenosine Receptor) antagonists able to avoid the undesirable side effects that have hampered their clinical development in the past years. The need to obtain potent and selective antagonists also derives from the evidence that antagonists may be more informative than agonists about the pathophysiological roles of specific adenosine receptors. In fact, agonists can activate receptors that are not activated by endogenous adenosine under specific conditions, whereas antagonists block (patho) physiological stimulation of the receptors. $A_3AR$ antagonists are receiving increasing interest as attractive therapeutic tools for the treatment of several pathological conditions of the central and peripheral nervous systems (CNS and PNS, respectively) (Moro S., Gao Z. G., Jacobson K. A., Spalluto G. Progress in the Pursuit of Therapeutic Adenosine Receptor Antagonists Med Res Rev. 26(2): 131-159, 2006).

One of the first therapeutic applications that was hypothesized for $A_3AR$ antagonists was the treatment of allergic conditions and inflammation. In fact, it was demonstrated that the activation of this receptor triggers in rodents the degranulation of mast cells and release of allergic mediators, such as histamine (Borea P. A., Gessi S., Bar-Yehuda S., Fishman P. $A_3$ adenosine receptor: pharmacology and role in disease. Handb. Exp. Pharmacol. 193, 297-327, 2009; Jacobson K. A., Gao, Z. G. Adenosine receptors as therapeutic targets. Nat. Rev. Drug Discov. 5, 247-264, 2006). $A_3AR$ activation increases aqueous humor secretion and thereby intraocular pressure in vivo through the regulation of chloride channels in non-pigmented ciliary epithelial cells. $A_3AR$ antagonists could be therefore a novel and safe approach for the treatment of glaucoma since it has been found, by in vivo experiments, that no ophthalmologic side effects such as appearance of eyelid closure and abnormality of the pupil were observed.

It has been demonstrated that $A_3AR$ is up regulated in renal stress, therefore the use of antagonists decreases the deposition of collagen, which at high concentrations leads to an increase in fibrous tissue and mesangial matrix, with consequent compression of the glomerular capillaries and consequent occlusion (Mailavaram R. P., Al-Attraqchi O. H. A, Kar S., Ghosh S. Current Status in the Design and Development of Agonists and Antagonists of Adenosine A3 Receptor as Potential Therapeutic Agents. Curr Pharm Des. 25(25):2772-2787, 2019).

Early studies indicated a protective effect of this receptor subtype during brain ischemia, but further evidence showed that acute $A_3AR$ stimulation exacerbates in vivo ischemic damage. Furthermore, $A_3ARs$ not only activate $G_i$ proteins but, under certain conditions, also activate $G_q$ proteins, which leads to an increase in intracellular calcium ions, triggering deleterious intracellular processes. This explains the neuroprotective effect observed by $A_3AR$ blockade (Coppi E., Cherchi F., Venturini M., Lucarini E., Corradetti R., Di Cesare Mannelli L., Ghelardini C., Pedata F., Pugliese A. M. Therapeutic Potential of Highly Selective $A_3$ Adenosine Receptor Ligands in the Central and Peripheral Nervous System. Molecules. 27, 1890, 2022).

Recently it has been proved that the $A_3AR$ is overexpressed in some tumor cell lines and promotes the activation of ERK1/2 and inhibition of Wnt signaling pathways, which are involved in the regulation of cancer cell proliferation. Although research data are controversial about the role of $A_3AR$ in this pathology, there is some evidence suggesting the use of $A_3AR$ antagonists in cancer therapy (Gessi S., Merighi S., Varani K., Cattabriga E., Benini A., Mirandola P., Leung E., Mac Lennan S., Feo C., Baraldi S, Borea P. A. Adenosine Receptors in Colon Carcinoma Tissues and Colon Tumoral Cell Lines: Focus on the $A_3$ Adenosine Subtype. J Cell Physiol. 211(3):826-36, 2007).

Indolizine represents a privileged scaffold for the development of bioactive compounds. Several synthetic indolizines have been reported to possess a broad spectrum of pharmacological activities, such as analgesic, anti-inflammatory (Venugopala K. N., Al-Attraqchi O. H., Tratrat C., Nayak S. K., Morsy M. A., Aldhubiab B. E., et al. Novel series of methyl 3-(substituted benzoyl)-7-substituted-2-phenylindolizine-1-carboxylates as promising anti-inflammatory agents: Molecular modeling studies. Biomolecules 9:661:2019), anticancer (Sandeep C., Padmashali B., Kulkarni R. S., Venugopala K. N., Venugopala R., Odhav B. Synthesis and characterization of ethyl 7-acetyl-2-substituted 3-(substituted benzoyl) indolizine-1-carboxylates for in vitro anticancer activity. Asian J Chem. 28:1043-48: 2016), antifungal (Uppar V., Chandrashekharappa S., Shivamallu C., Kollur S. P., Ortega-Castro J., Frau J., et al. Investigation of antifungal properties of synthetic dimethyl-4-bromo-1-(substituted benzoyl) pyrrolo[1, 2-a] quinoline-2, 3-dicarboxylates analogues Molecular docking studies and conceptual dft-based chemical reactivity descriptors and pharmacokinetics evaluation. Molecules 26; 2722:2021), antidiabetic, antihistaminic, COX-2 inhibition (Chandrashekharappa S., Venugopala K. N., Tratrat C., Mahomoodally F. M., Aldhubiab B. E., Haroun M., et al. Efficient synthesis and characterization of novel indolizines: Exploration of in vitro cox-2 inhibitory activity and molecular modelling studies. New J Chem. 42:4893-01, 2018), antitubercular (Venugopala K. N., Chandrashekharappa S., Deb P. K., Tratrat C., Pillay M., Chopra D., et al. Anti-tubercular activity and molecular docking studies of indolizine derivatives targeting mycobacterial inha enzyme. J Enzyme Inhib Med Chem. 36:1471-86:2021), antileishmanic, antimicrobial (Uppar V., Nagaraju K. K., Basarikatti A. I., Chougala M., Chandrashekharappa S., Mohan M. K., et al. Microwave induced synthesis, and pharmacological properties of novel 1-benzoyl-4-bromopyrrolo[1, 2-a] quinoline-3-carboxylate analogues. Chemical Data Collections 25:100316: 2020), antimutagenic, antioxidant (Uppar V., Chandrashekharappa S., Mohan M. K., Basarikattia A. I., Rachotimath B. B., Chougala M., et al. Synthesis and characterization of indolizine and 5, 6-benzo-fused indolizine derivatives with their pharmacological applications. Chemical Data Collections 29:100524:2020), antiviral, larvicidal (Sandeep C., Venugopala K. N., Nayak S. K., Raquel M. G., Daniel A. G., Kumalo H. M., et al. One-pot microwave assisted synthesis and structural elucidation of novel ethyl 3-substituted-7-methylindolizine-1-carboxylates with larvicidal activity against *anopheles arabiensis*. J Mol Struct. 1156:377-84:

2018), herbicidal and α7 nAChR inhibitors, anti-alzheimer, antischizophrenic, anticonvulsant and inhibitors of various enzymes.

Thus, compounds having high adenosine receptor activity solving the aforementioned problems are desired.

SUMMARY

The present subject matter relates to the use of certain 1,2,3,6,8-pentasubstituted indolizines as adenosine receptor modulators. As such, the present methods may be used for treating a variety of therapeutic applications, including but not limited to one or more of cardiovascular diseases or disorders, respiratory diseases or disorders, inflammation, neurodegenerative diseases, and cancer.

In an embodiment, the present subject matter relates to methods of using the compounds described herein for modulating activity of one or more adenosine receptors, including but not limited to one or more of the $A_1AR$, $A_2AR$, and $A_3AR$ adenosine receptor subtypes. In an embodiment, the present subject matter relates to methods of using the present compounds as $A_3AR$ antagonists, making them useful in the treatment of a number of pathological conditions of the central and peripheral nervous systems, such as but not limited to brain ischemia, glaucoma, allergy, renal fibrosis, tumor, and the like.

In an embodiment, the present subject matter relates to method of inhibiting adenosine receptor activity in a patient, comprising administering to a patient in need thereof a therapeutically effective amount a compound having the formula I:

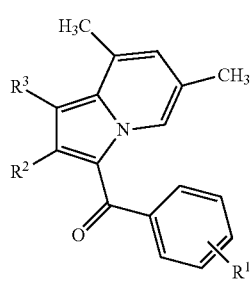

I wherein:
R$^1$ is selected from the group consisting of 4-OCH$_3$, 4-Cl, 4-Br, 4-F, 2-NO$_2$, 3,5-CF$_3$, CN, and CH$_3$;
R$^2$ is COOCH$_3$ or COOC$_2$H$_5$; and
R$^3$ is H or COOCH$_3$.

In another embodiment, the present subject matter relates to a method of treating one or more pathological conditions of the central and peripheral nervous systems in a patient, comprising administering to a patient in need thereof a therapeutically effective amount a compound having the formula I:

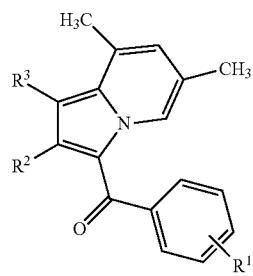

I wherein:
R$^1$ is selected from the group consisting of 4-OCH$_3$, 4-Cl, 4-Br, 4-F, 2-NO$_2$, 3,5-CF$_3$, CN, and CH$_3$;
R$^2$ is COOCH$_3$ or COOC$_2$H$_5$; and
R$^3$ is H or COOCH$_3$.

In an embodiment, the present subject matter relates to a method of inhibiting adenosine receptor activity in a patient, comprising administering to a patient in need thereof a therapeutically effective amount a compound selected from the group consisting of: Ethyl 3-(4-chlorobenzoyl)-6,8-dimethylindolizine-1-carboxylate (KNV1); Dimethyl 3-(4-methoxybenzoyl)-6,8-dimethylindolizine-1,2-dicarboxylate (KNV2); Ethyl 3-(4-bromobenzoyl)-6,8-dimethylindolizine-1-carboxylate (KNV3); Dimethyl 3-(4-bromobenzoyl)-6,8-dimethylindolizine-1,2-dicarboxylate (KNV4); Ethyl 3-(4-fluorobenzoyl)-6,8-dimethylindolizine-1-carboxylate (KNV5); Ethyl 6,8-dimethyl-3-(2-nitrobenzo yl)indolizine-1-carboxylate (KNV6); Ethyl 6,8-dimethyl-3-(4-methylbenzoyl)indolizine-1-carboxylate (KNV7); Dimethyl 6,8-dimethyl-3-(4-methylbenzoyl)indolizine-1,2-dicarboxylate (KNV8); Ethyl 3-(4-methoxybenzoyl)-6,8-dimethylindolizine-1-carboxylate (KNV9); Dimethyl 3-(4-chlorobenzoyl)-6,8-dimethylindolizine-1,2-dicarboxylate (KNV10); Ethyl 3-(4-cyanobenzoyl)-6,8-dimethylindolizine-1-carboxylate (KNV11); Dimethyl 3-(4-cyanobenzoyl)-6,8-dimethylindolizine-1,2-dicarboxylate (KNV12); and Ethyl 3-(3,5-bis (trifluoromethyl)benzoyl)-6,8-dimethylindolizine-1-carboxylate (KNV13).

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to method of inhibiting adenosine receptor activity in a patient, comprising administering to a patient in need thereof a therapeutically effective amount a compound having the formula I:

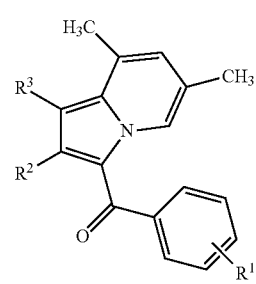

wherein:

$R^1$ is selected from the group consisting of 4-OCH$_3$, 4-Cl, 4-Br, 4-F, 2-NO$_2$, 3,5-CF$_3$, CN, and CH$_3$;

$R^2$ is COOCH$_3$ or COOC$_2$H$_5$; and $R^3$ is H or COOCH$_3$.

In an embodiment, the compound used in the present methods can be selected from the group consisting of: Ethyl 3-(4-chlorobenzoyl)-6,8-dimethylindolizine-1-carboxylate (KNV1); Dimethyl 3-(4-methoxybenzoyl)-6,8-dimethylindolizine-1,2-dicarboxylate (KNV2); Ethyl 3-(4-bromobenzoyl)-6,8-dimethylindolizine-1-carboxylate (KNV3); Dimethyl 3-(4-bromobenzoyl)-6,8-dimethylindolizine-1,2-dicarboxylate (KNV4); Ethyl 3-(4-fluorobenzoyl)-6,8-dimethylindolizine-1-carboxylate (KNV5); Ethyl 6,8-dimethyl-3-(2-nitrobenzoyl)indolizine-1-carboxylate (KNV6); Ethyl 6,8-dimethyl-3-(4-methylbenzoyl)indolizine-1-carboxylate (KNV7); Dimethyl 6,8-dimethyl-3-(4-methylbenzoyl)indolizine-1,2-dicarboxylate (KNV8); Ethyl 3-(4-methoxybenzoyl)-6,8-dimethylindolizine-1-carboxylate (KNV9); Dimethyl 3-(4-chlorobenzoyl)-6,8-dimethylindolizine-1,2-dicarboxylate (KNV10); Ethyl 3-(4-cyanobenzoyl)-6,8-dimethylindolizine-1-carboxylate (KNV11); Dimethyl 3-(4-cyanobenzoyl)-6,8-dimethylindolizine-1,2-dicarboxylate (KNV12); and Ethyl 3-(3,5-bis(trifluoromethyl)benzoyl)-6,8-dimethylindolizine-1-carboxylate (KNV13).

Said differently, the compounds of formula I used in the present methods can be selected from the group consisting of:

| Compound Code | Chemical Structure |
|---|---|
| KNV1 | 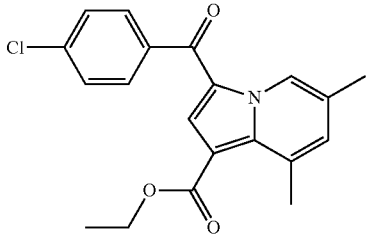 [SMILES: CCOC(=O)c1cc(C(=O)c2ccc(Cl)cc2)n2cc(C)cc(C)c12] |
| KNV2 | 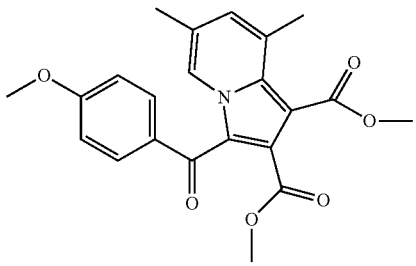 |
| KNV3 | 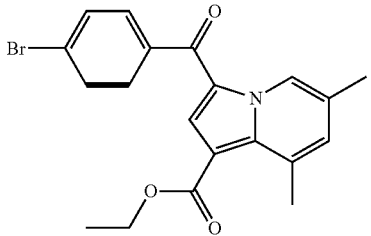 |
| KNV4 | 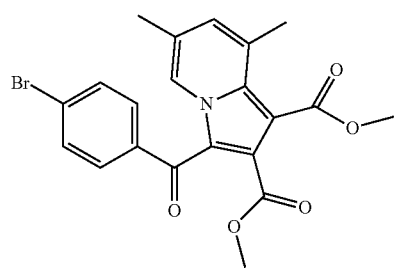 [SMILES: COC(=O)c1c(C(=O)OC)c2c(C)cc(C)cn2c1C(=O)c1ccc(Br)cc1] |
| KNV5 | 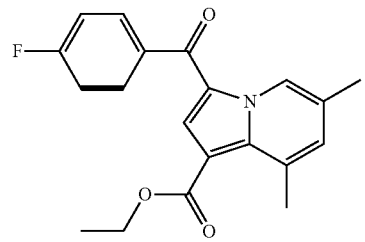 |
| KNV6 | 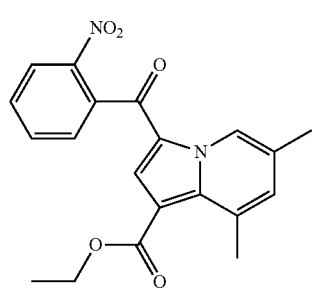 [SMILES: CCOC(=O)c1cc(C(=O)c2ccccc2[N+](=O)[O-])n2cc(C)cc(C)c12] |
-continued
| Compound Code | Chemical Structure |
|---|---|
| KNV7 | 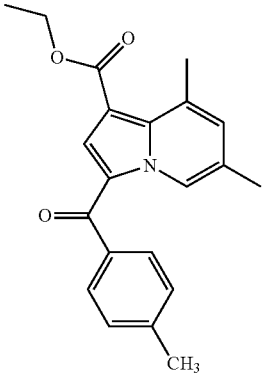 [SMILES: CCOC(=O)c1cc(C(=O)c2ccc(C)cc2)n2cc(C)cc(C)c12] |
| KNV8 | 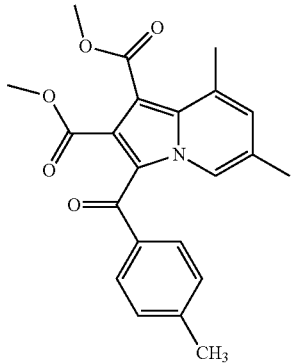 |
| KNV9 | 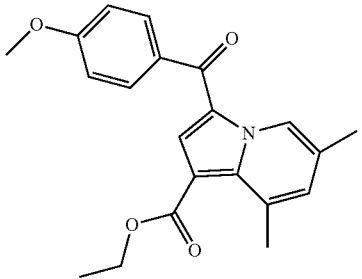 |
| KNV10 | 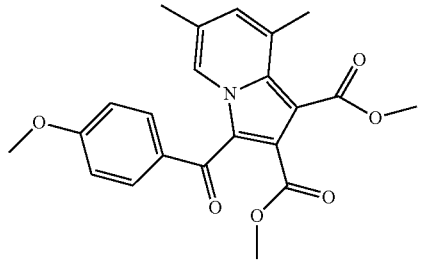 |

-continued

| Compound Code | Chemical Structure |
|---|---|
| KNV11 | 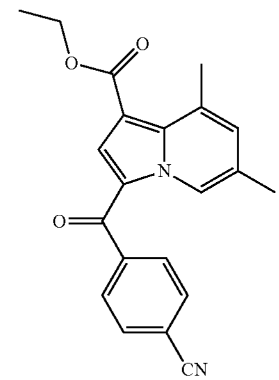 [SMILES: CCOC(=O)c1cc(C(=O)c2ccc(C#N)cc2)n2cc(C)cc(C)c12] |
| KNV12 | 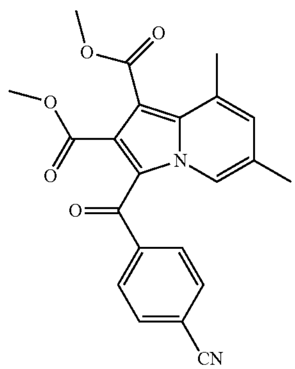 |
| KNV13 | 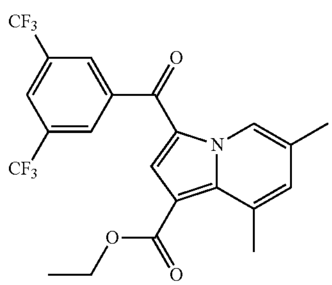 [SMILES: CCOC(=O)c1cc(C(=O)c2cc(C(F)(F)F)cc(C(F)(F)F)c2)n2cc(C)cc(C)c12] |

In an embodiment, the adenosine receptor inhibited or modulated herein can be selected from the group consisting of $hA_1AR$, $hA_2AR$, $hA_3AR$, and a combination thereof. In another embodiment, the adenosine receptor can be $hA_3AR$. In a further embodiment, the adenosine receptor $hA_2AR$ can have a subtype selected from the group consisting of $hA_{2A}AR$, $hA_{2B}AR$, and a combination thereof.

One of the aspects of the present subject matter is the therapeutic properties these compounds show for the treatment of pathological conditions or diseases that can be improved by $A_3AR$ modulation. The $G_i$-coupled $A_3AR$ mediates anti-inflammatory, anticancer, and anti-ischemic protective effects. Under physiological conditions, adenosine is found at low concentrations (nanomolar range), while in stress or hypoxic conditions its concentration increases (micromolar range). The $A_3AR$ is overexpressed in inflammatory and cancer cells, while low expression is found in normal cells, rendering the $A_3AR$ as a therapeutic target.

Ligands of the $G_i$ protein coupled $A_3AR$ are attractive therapeutic tools for the treatment of a number of pathological conditions of the central and peripheral nervous systems (CNS and PNS, respectively). Their safe pharmacological profiles emerge from clinical trials on different pathologies such as rheumatoid arthritis, psoriasis, and fatty liver diseases. In addition, $A_3AR$ ligands proved to be effective in preclinical animal models of brain ischemia and in hippocampal slices, useful for the treatment of stroke. Valuable evidence from rodent models of chronic pain indicates the possible use of selective $A_3AR$ ligands as non-narcotic anti-hyperalgesic agents for pain control.

In certain embodiments of the present subject matter, the inhibiting the adenosine receptor activity in the patient can result in the treatment of one or more diseases, disorders, or conditions selected from the group consisting of cardiovascular diseases or disorders, respiratory diseases or disorders, inflammatory diseases, disorders, or conditions, neurodegenerative diseases, cancer, and any combination thereof.

In other embodiments, the inhibiting the adenosine receptor activity in the patient can result in the treatment of one or more pathological conditions of the central and peripheral nervous systems.

In this regard, the one or more pathological conditions of the central and peripheral nervous systems treatable herein can be selected from the group consisting of allergies, inflammation, glaucoma, brain ischemia, renal fibrosis, cancer, rheumatoid arthritis, psoriasis fatty liver diseases, stroke, pain, and any combination thereof.

In another embodiment, the present subject matter relates to a method of treating one or more pathological conditions of the central and peripheral nervous systems in a patient, comprising administering to a patient in need thereof a therapeutically effective amount a compound having the formula I:

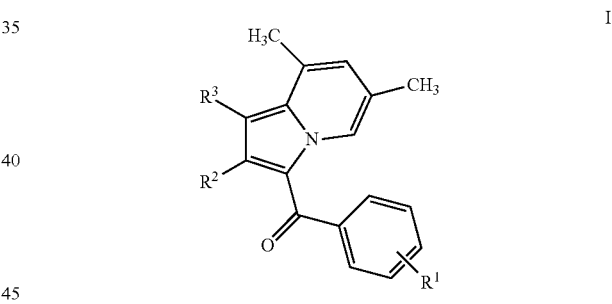

wherein:
R$^1$ is selected from the group consisting of 4-OCH$_3$, 4-Cl, 4-Br, 4-F, 2-NO$_2$, 3,5-CF$_3$, CN, and CH$_3$;
R$^2$ is COOCH$_3$ or COOC$_2$H$_5$; and
R$^3$ is H or COOCH$_3$.

In an embodiment, the present subject matter relates to a method of inhibiting adenosine receptor activity in a patient, comprising administering to a patient in need thereof a therapeutically effective amount a compound selected from the group consisting of: Ethyl 3-(4-chlorobenzoyl)-6,8-dimethylindolizine-1-carboxylate (KNV1); Dimethyl 3-(4-methoxybenzoyl)-6, 8-dimethylindolizine-1,2-dicarboxylate (KNV2); Ethyl 3-(4-bromobenzoyl)-6, 8-dimethylindolizine-1-(KNV3); Dimethyl 3-(4-bromobenzoyl)-6, 8-dimethylindolizine-1,2-dicarboxylate (KNV4); Ethyl Ethyl 3-(4-fluorobenzoyl)-6,8-dimethylindolizine-1-carboxylate (KNV5); Ethyl 6,8-dimethyl-3-(2-nitrobenzoyl) indolizine-1-carboxylate (KNV6); Ethyl 6,8-dimethyl-3-(4-methylbenzoyl)indolizine-1-carboxylate (KNV7); Dimethyl 6,8-dimethyl-3-(4-methylbenzoyl)indolizine-1,2-dicarboxylate (KNV8); Ethyl 3-(4-methoxybenzoyl)-6,8-dimethylindolizine-1-carboxylate (KNV9); Dimethyl 3-(4-chlorobenzoyl)-6,8-dimethylindolizine-1,2-dicarboxylate (KNV10); Ethyl 3-(4-cyanobenzoyl)-6, 8-dimethylindolizine-1-carboxylate (KNV11); Dimethyl 3-(4-cyanobenzoyl)-6,8-dimethylindolizine-1,2-dicarboxylate (KNV12); and Ethyl 3-(3, 5-bis(trifluoromethyl)benzoyl)-6,8-dimethylindolizine-1-carboxylate (KNV13).

It is to be understood that the present subject matter covers all combinations of substituent groups, compounds, and indications referred to herein.

The present compounds were obtained by structural modifications of the indolizine scaffold.

In another embodiment, the present methods can be carried out by administration of a pharmaceutical composition comprising a present compound(s) and a pharmaceutically acceptable carrier. Pharmaceutical compositions comprising one or more of the present compounds and a pharmaceutically acceptable carrier may be made using any technique generally known in the art. As a non-limiting example, a method of making a pharmaceutical composition includes mixing one or more of the present compounds with a pharmaceutically acceptable carrier. For example, the method of making a pharmaceutical composition can include mixing the present compound under sterile conditions with a pharmaceutically acceptable carrier with preservatives, buffers, and/or propellants to create the pharmaceutical composition.

The present subject matter further relates to a pharmaceutical composition, which comprises at least one of the present compounds together with at least one pharmaceutically acceptable auxiliary.

An embodiment of the present subject matter is directed to a method of treatment, comprising administering to a subject in need thereof a therapeutically effective amount of the pharmaceutical composition according to the present subject matter. A therapeutically effective amount of the pharmaceutical composition or an amount effective to treat a disease may be determined initially from the Examples described herein and adjusted for specific targeted diseases using routine methods.

The present compounds or pharmaceutical compositions thereof can be administered to a subject by any suitable route. For example, the compositions can be administered nasally, rectally, intracisternally, intraperitoneally, transdermally (as by powders, ointments, or drops), and/or parenterally.

The present compounds have valuable pharmaceutical properties, which make them commercially utilizable. Accordingly, the present subject matter further relates to use of the present compounds for the treatment of diseases such as cancers. Similarly, the present compounds can be used to inhibit and/or modulate adenosine receptor activity in a patient.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The present subject matter can be better understood by referring to the following examples.

EXAMPLES

Example 1

Preparation of methyl 3-substitutedbenzoyl-1-ethyl-6,8-dimethylindolizine-2-carboxylate (KNV1-KNV13)

Compounds KNV1-KNV13 were synthesized, purified by column chromatography, and well characterized by FT-IR, NMR, LC-MS, and elemental analysis. The purity of the compounds was 99% as measured by HPLC.

Intermediates to obtain the present compounds were obtained by stirring a mixture of 3,5-dimethylpyridine, and para-substituted phenacyl bromides in a dry acetone medium at 5 h. Further reaction with diethyl 2-butynedioate/1-ethyl 4-methyl but-2-ynedioate in the presence of water with continuous stirring at 80° C. for 3 h resulted in the formation of the present compounds. The resulting compounds were purified using ethyl acetate and hexane as an eluent by column chromatography, and compound purity was found to be more than 99% with a satisfactory yield (69% to 83%). The chemical structures of the newly synthesized compounds were ascertained with the help of spectroscopic techniques, such as FT-IR, NMR ($^1$H and $^{13}$C), LC-MS, and elemental analysis. In LC-MS, the molecular ion peaks of these compounds were in good agreement with their proposed molecular masses. Elemental analysis results of the title compounds were within ±0.4% of the calculated values.

Example 2

General Procedure for the Preparation of methyl 3-substitutedbenzoyl-1-ethyl-6,8-dimethylindolizine-2-carboxylate (KNV1-KNV13)

To a stirred solution of 1-(2-(4-methoxy/chloro/bromo/fluoro/2-nitro/3,5-trifluoromethyl/4-nitrile/methyl-phenyl)-2-oxoethyl) pyridin-1-ium bromide (3a/3b/3c/3d/3e/3f/3g/3h) (0.0016 mol), in water (10 mL), was added substituted diethyl 2-butynedioate/1-ethyl 4-methyl but-2-ynedioate (0.0016 mol), stirred at 80° C. for 3 h. Completion of the reaction was monitored by TLC. The reaction mixture was diluted with ethyl acetate. The organic layer was separated, washed with brine, and dried under sodium sulfate. The crude compound was purified by recrystallization method using hexane and ethyl acetate to afford 73-89% yield of dimethyl 3-(substitutedbenzoyl)-6,8-dimethylindolizine-1,2-dicarboxylate (KNV1-KNV13). The characterization details of title compounds KNV1-KNV13 are reported below.

Ethyl 3-(4-chlorobenzoyl)-6,8-dimethylindolizine-1-carboxylate (KNV1). $^1$H NMR (400 MHz, CDCl$_3$) δ 9.76 (s, 1H), 7.77 (d, J=8.1 Hz, 2H), 7.73 (s, 1H), 7.51 (d, J=8.0 Hz, 2H), 7.12 (s, 1H), 4.36-4.31 (q, J=7.1 Hz, 2H), 2.80 (s, 3H), 2.41 (s, 3H), 1.40-1.36 (t, J=7.1 Hz, 3H); $^{13}$C NMR (100 MHz, CDCl$_3$) δ 183.72, 163.99, 138.67, 137.80, 137.54, 132.33, 131.35, 130.58, 130.39, 129.23, 128.63, 125.23, 125.15, 121.24, 108.22, 60.39, 21.79, 18.27, 14.46.

Dimethyl 3-(4-methoxybenzoyl)-6,8-dimethylindolizine-1,2-dicarboxylate (KNV2). $^1$H NMR (400 MHz, CDCl$_3$) δ

8.90 (s, 1H), 7.73 (d, J=8.1 Hz, 2H), 7.29 (s, 1H), 7.29 (s, 1H), 6.95-6.92 (m, 2H), 3.88 (s, 3H), 3.87 (s, 3H), 3.33 (s, 3H), 2.58 (s, 3H), 2.32 (s, 3H); $^{13}$C NMR (100 MHz, CDCl$_3$) δ 185.85, 165.31, 165.06, 163.01, 133.71, 133.01, 131.13, 129.76, 128.76, 127.49, 124.88, 122.90, 120.70, 113.55, 107.28, 55.50, 52.24, 52.01, 20.18, 18.36, 18.30.

Ethyl 3-(4-bromobenzoyl)-6,8-dimethylindolizine-1-carboxylate (KNV3). $^1$H NMR (400 MHz, CDCl$_3$) δ 9.76 (s, 1H), 7.69 (dd, J=17.0, 7.5 Hz, 5H), 7.12 (s, 1H), 4.36-4.31 (q, J=7.1 Hz, 2H), 2.81 (s, 3H), 2.41 (s, 3H), 1.40-1.37 (t, J=7.1 Hz, 3H); $^{13}$C NMR (100 MHz, CDCl$_3$) δ 183.79, 163.97, 139.13, 137.81, 132.35, 131.59, 130.58, 130.55, 129.24, 125.99, 125.25, 125.15, 121.20, 108.26, 60.39, 21.79, 18.27, 14.46.

Dimethyl 3-(4-bromobenzoyl)-6,8-dimethylindolizine-1,2-dicarboxylate (KNV4). $^1$H NMR (400 MHz, CDCl$_3$) δ 9.13 (s, 1H), 7.50 (m, 4H), 6.92 (s, 1H), 3.78 (s, 3H), 3.23 (s, 3H), 2.50 (s, 3H), 2.27 (s, 3H); $^{13}$C NMR (100 MHz, CDCl$_3$) δ 185.49, 168.35, 164.92, 164.89, 142.40, 139.30, 138.65, 134.31, 132.60, 131.67, 131.52, 131.47, 130.79, 130.21, 128.99, 128.92, 127.74, 126.72, 125.68, 123.40, 119.69, 107.97, 52.31, 52.09, 20.25, 18.62, 18.42, 18.38.

Ethyl 3-(4-fluorobenzoyl)-6,8-dimethylindolizine-1-carboxylate (KNV5). $^1$H NMR (400 MHz, CDCl$_3$) δ 9.75 (s, 1H), 7.84 (dd, J=8.0, 5.7 Hz, 2H), 7.73 (s, 1H), 7.22 (t, J=8.5 Hz, 2H), 7.11 (s, 1H), 4.36-4.31 (q, J=7.1 Hz, 2H), 2.80 (s, 3H), 2.41 (s, 3H), 1.40-1.36 (t, J=7.1 Hz, 3H); $^{13}$C NMR (100 MHz, CDCl$_3$) δ 183.70, 165.94, 164.04, 163.44, 137.72, 136.50, 136.47, 132.20, 131.37, 131.29, 130.51, 129.19, 125.10, 121.33, 115.54, 115.32, 108.07, 60.36, 21.80, 18.27, 14.45.

Ethyl 6,8-dimethyl-3-(2-nitrobenzoyl)indolizine-1-carboxylate (KNV6). $^1$H NMR (400 MHz, CDCl$_3$) δ 9.83 (s, 1H), 8.24 (d, J=8.2 Hz, 1H), 7.79 (t, J=7.5 Hz, 1H), 7.70 (t, J=7.8 Hz, 1H), 7.60 (d, J=7.5 Hz, 1H), 7.36 (s, 1H), 7.16 (s, 1H), 4.31-4.26 (q, J=7.1 Hz, 2H), 2.79 (s, 3H), 2.44 (s, 3H), 1.35-1.32 (t, J=7.1 Hz, 3H); $^{13}$C NMR (100 MHz, CDCl$_3$) δ 181.29, 163.77, 146.91, 138.00, 136.34, 133.68, 132.79, 130.32, 129.71, 129.44, 129.38, 125.77, 125.40, 124.79, 121.04, 108. 60.40, 21.80, 18.25, 14.39.

Ethyl 6,8-dimethyl-3-(4-methylbenzoyl)indolizine-1-carboxylate (KNV7). $^1$H NMR (400 MHz, CDCl$_3$) δ 9.67 (s, 1H), 7.68 (s, 1H), 7.65-7.63 (d, J=8.1 Hz, 2H), 7.25-7.23 d, J=8.1 Hz, 2H), 6.99 (s, 1H), 4.26-4.20 (q, J=7.1 Hz, 2H), 2.81 (s, 3H), 2.34 (s, 3H), 2.26 (s, 3H). 1.30-1.26 (t, J=7.1 Hz, 3H); $^{13}$C NMR (100 MHz, CDCl$_3$) δ 185.10, 169.66, 164.17, 162.66, 143.92, 141.86, 137.57, 131.92, 130.52, 130.09, 129.19, 129.08, 129.00, 128.45, 127.21, 125.09, 124.84, 121.66, 107.74, 60.26, 36.54, 31.48, 21.82, 21.70, 21.58, 18.26, 14.46.

Dimethyl 6,8-dimethyl-3-(4-methylbenzoyl)indolizine-1,2-dicarboxylate (KNV8). $^1$H NMR (400 MHz, CDCl$_3$) δ 9.12 (s, 1H), 7.62 (d, J=8.1 Hz, 2H), 7.29-7.24 (3, 2H), 7.29 (s, 1H), 6.95 (s, 1H), 3.87 (s, 3H), 3.26 (s, 3H), 2.58 (s, 3H), 2.43 (s, 3H), 2.34 (s, 3H); $^{13}$C NMR (100 MHz, CDCl$_3$) δ 186.72, 165.17, 165.03, 142.74, 137.77, 133.93, 130.15, 129.49, 129.16, 128.92, 128.77, 128.34, 125.12, 123.16, 120.48, 107.45, 52.23, 51.89, 21.72, 21.62, 20.23, 18.38.

Ethyl 3-(4-methoxybenzoyl)-6,8-dimethylindolizine-1-carboxylate (KNV9). $^1$H NMR (400 MHz, CDCl$_3$) δ 9.71 (s, 1H), 7.85 (d, J=8.1 Hz, 2H), 7.78 (s, 1H), 7.29 (s, 1H), 7.13-6.98 (m, 3H), 4.33 (q, J=7.1 Hz, 2H), 3.93 (s, 3H), 2.80 (s, 3H), 2.39 (s, 3H), 1.38 (t, J=7.1 Hz, 3H); $^{13}$C NMR (100 MHz, CDCl$_3$) δ 184.29, 162.39 131.75, 131.24, 130.11, 129.07, 125.00, 124.68, 121.70, 113.68, 60.26, 55.48, 21.84, 18.26, 14.47.

Dimethyl 3-(4-chlorobenzoyl)-6,8-dimethylindolizine-1,2-dicarboxylate (KNV10). $^1$H NMR (400 MHz, CDCl$_3$) δ 9.21 (s, 1H), 7.66 (d, J=7.8 Hz, 2H), 7.44 (d, J=7.6 Hz, 2H), 7.01 (s, 1H), 3.87 (s, 3H), 3.32 (s, 3H), 2.60 (s, 3H), 2.36 (s, 2H); $^{13}$C NMR (100 MHz, CDCl$_3$) δ 185.39, 164.94, 164.89, 145.16, 138.86, 138.22, 134.28, 131.36, 130.73, 130.09, 128.91, 128.65, 128.50, 125.64, 123.37, 119.76, 107.94, 52.30, 52.07, 20.24, 18.41, 18.30.

Ethyl 3-(4-cyanobenzoyl)-6,8-dimethylindolizine-1-carboxylate (KNV11). $^1$H NMR (400 MHz, CDCl$_3$) δ 9.80 (1H, s), 7.89 (2H, d, J=8.0 Hz), 7.84 (2H, d, J=7.9 Hz), 7.67 (1H, s), 7.17 (1H, s), 4.36-4.31 (2H, q, J=7.1 Hz), 2.81 (3H, s), 2.43 (3H, s), 1.40-1.36 (3H, t, J=7.1 Hz); $^{13}$C NMR (100 MHz, CDCl$_3$) δ 182.74, 163.79, 144.20, 138.07, 132.90, 132.24, 130.82, 129.40, 129.35, 125.75, 125.30, 120.86, 118.25, 114.61, 108.89, 60.52, 21.76, 18.29, 14.44.

Dimethyl 3-(4-cyanobenzoyl)-6,8-dimethylindolizine-1,2-dicarboxylate (KNV12). $^1$H NMR (400 MHz, CDCl$_3$) δ 9.37 (1H, s), 7.82-7.67 (4H, m), 7.08 (1H, s), 3.87 (3H, s), 3.29 (3H, s), 2.61 (3H, s), 2.40 (3H, s); $^{13}$C NMR (100 MHz, CDCl$_3$) δ 164.68, 131.96, 131.53, 129.06, 123.74, 77.35, 77.03, 76.71, 52.38, 52.12, 20.25, 18.45.

Ethyl 3-(3,5-bis(trifluoromethyl)benzoyl)-6,8-dimethylindolizine-1-carboxylate (KNV13). $^1$H NMR (400 MHz, CDCl$_3$) δ 9.79 (s, 1H), 8.49 (s, 1H), 8.24 (s, 1H), 8.05 (d, J=38.4 Hz, 1H), 7.68 (s, 1H), 7.24 (d, J=38.4 Hz, 1H), 4.34 (q, 3H), 2.83 (s, 3H), 2.43 (s, 3H), 1.38 (t, 3H); $^{13}$C NMR (100 MHz, CDCl$_3$) δ 181.10, 167.41, 163.63, 142.18, 138.27, 133.13, 132.06, 131.72, 130.87, 129.82, 129.54, 128.95, 125.97, 125.31, 124.50, 120.51, 109.26, 60.54, 21.73, 18.31, 14.29.

Example 3

Adenosine Receptor Activity

The activity of the present compounds was evaluated using the GloSensor™ cAMP assay, which is a new non-radioactive method offering a simple approach to monitor GPCR activity through changes in the intracellular cAMP concentration. This assay uses a mutant form of Photinus pyralis luciferase into which a cAMP-binding protein moiety has been inserted. The binding with cAMP triggers a biosensor conformational change that leads to an increase of light output allowing to evaluate the activity of ligands at the receptor under study. Following pre-equilibration with a substrate, cells stably expressing both the receptor of interest and the biosensor can be used to evaluate GPCR function enabling easy kinetic measurements of cAMP accumulation or turnover in living cells.

The antagonist profile of the compounds on $A_{2B}AR$ was evaluated by assessing their ability to counteract the agonist NECA-induced increase of cAMP accumulation. After 2 hrs of equilibration in reaction medium cells were incubated in 384 well plate (10 min at room temperature) with 3 μl of different antagonist concentrations and then treated with 3 μl of a fixed dose of NECA. After further 10 minutes of incubation various luminescence reads were performed at different incubation times.

The antagonist profile of the compounds on $A_3AR$ was studied by assessing their ability to counteract the NECA-induced decrease of cAMP accumulation. After 2 hrs of equilibration in reaction medium the cells were incubated in a 384 well plate (10 min at room temperature) with 3 μl of different antagonist concentrations and then treated with 3 μl of a fixed dose of agonist. 1 μl of Forskolin 500 μM, final concentration 10 μM, were added 10 minutes after agonist and various luminescence reads were performed at different incubation times.

Table 1 below reports the affinity and antagonist values of compounds KNV1-KNV13. In particular, the binding affinity is expressed in $K_i$ and the antagonistic activity in $IC_{50}$.

TABLE 1

| Compound Code | Chemical Structure | IUPAC Nomenclature | $hA_1R$ ($K_i$ nM)[a] | $hA_{2A}R$ ($K_i$ nM)[b] | $hA_{2B}R$ ($IC_{50}$ nM)[c] | $hA_3R$ ($K_i$ nM)[d] | $hA_{2A}R$ ($IC_{50}$ nM)[e] |
|---|---|---|---|---|---|---|---|
| KNV1 | 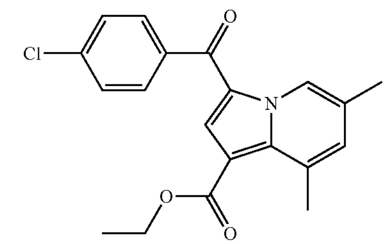 [SMILES: CCOC(=O)c1cc(C(=O)c2ccc(Cl)cc2)n2cc(C)cc(C)c12] | Ethyl 3-(4-chlorobenzoyl)-6,8-dimethylindolizine-1-carboxylate | >30000 | >30000 | >30000 | 591 ± 112 | 1514 ± 351 |
| KNV2 | 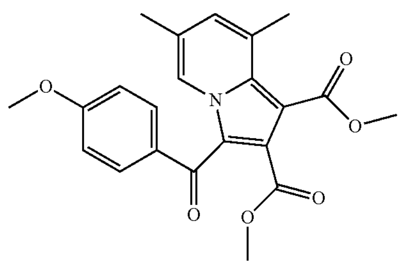 | Dimethyl 3-(4-methoxybenzoyl)-6,8-dimethylindolizine-1,2-dicarboxylate | 1328 ± 217 | 4815 ± 243 | >30000 | 1914 ± 45 | 7895 ± 1085 |
| KNV3 | 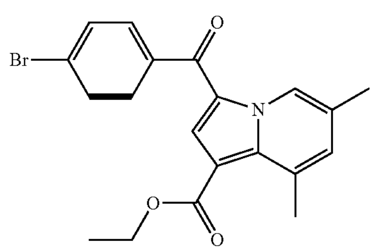 | Ethyl 3-(4-bromocyclohexa-1,3-diene-1-carbonyl)-6,8-dimethylindolizine-1-carboxylate | >30000 | >30000 | >30000 | >30000 | >30000 |
| KNV4 | 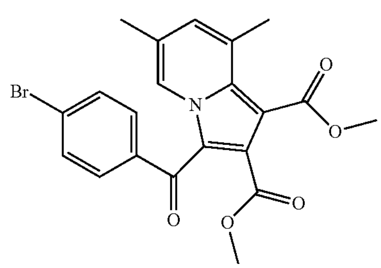 [SMILES: COC(=O)c1c(C(=O)OC)c2c(C)cc(C)cn2c1C(=O)c1ccc(Br)cc1] | Dimethyl 3-(4-bromobenzoyl)-6,8-dimethylindolizine-1,2-dicarboxylate | 6976 ± 330 | 5537 ± 998 | >30000 | 2164 ± 468 | 9581 ± 1085 |
| KNV5 | 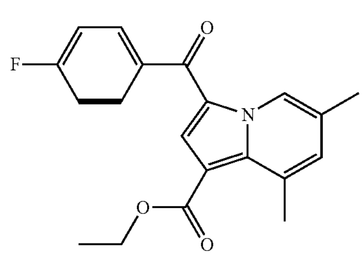 | Ethyl 3-(4-fluorocyclohexa-1,3-diene-1-carbonyl)-6,8-dimethylindolizine-1-carboxylate | >30000 | >30000 | >30000 | 213 ± 16 | 196 ± 55 |

TABLE 1-continued

| Compound Code | Chemical Structure | IUPAC Nomenclature | hA$_1$R (K$_i$ nM)$^a$ | hA$_{2A}$R (K$_i$ nM)$^b$ | hA$_{2B}$R (IC$_{50}$ nM)$^c$ | hA$_3$R (K$_i$ nM)$^d$ | hA$_{2A}$R (IC$_{50}$ nM)$^e$ |
|---|---|---|---|---|---|---|---|
| KNV6 | 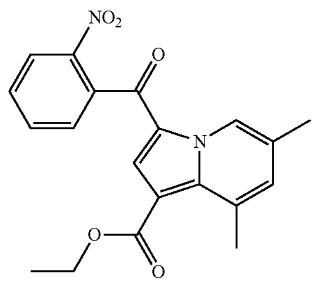 [SMILES: CCOC(=O)c1cc(C(=O)c2ccccc2[N+](=O)[O-])n2cc(C)cc(C)c12] | Ethyl 6,8-dimethyl-3-(2-nitrobenzoyl)indolizine-1-carboxylate | >30000 | 7967 ± 1658 | >30000 | 930 ± 159 | 3425 ± 879 |
| KNV7 | 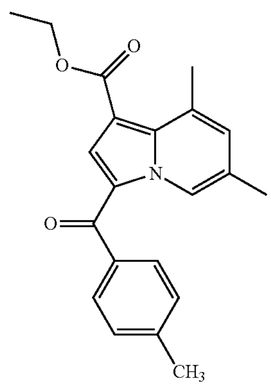 [SMILES: CCOC(=O)c1cc(C(=O)c2ccc(C)cc2)n2cc(C)cc(C)c12] | Ethyl 6,8-dimethyl-3-(4-methylbenzoyl)indolizine-1-carboxylate | >30000 | 4973 ± 508 | >30000 | 1070 ± 157 | 4210 ± 1151 |
| KNV8 | 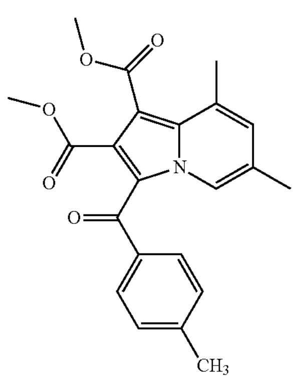 | Dimethyl 6,8-dimethyl-3-(4-methylbenzoyl)indolizine-1,2-dicarboxylate | 2393 ± 171 | 1609 ± 13 | >30000 | 3090 ± 6 | 11041 ± 2051 |
| KNV9 | 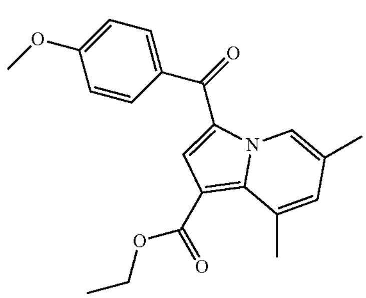 | Ethyl 3-(4-methoxybenzoyl)-6,8-dimethylindolizine-1-carboxylate | >30000 | >30000 | >30000 | 305 ± 57 | 865 ± 105 |

TABLE 1-continued

| Compound Code | Chemical Structure | IUPAC Nomenclature | hA$_1$R (K$_i$ nM)[a] | hA$_{2A}$R (K$_i$ nM)[b] | hA$_{2B}$R (IC$_{50}$ nM)[c] | hA$_3$R (K$_i$ nM)[d] | hA$_{2A}$R (IC$_{50}$ nM)[e] |
|---|---|---|---|---|---|---|---|
| KNV10 | 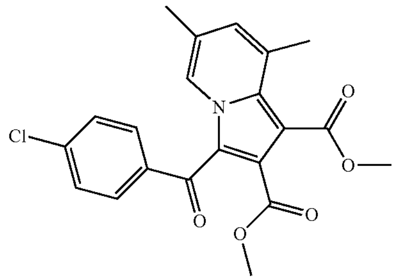 [SMILES: COC(=O)c1c(C(=O)OC)c2c(C)cc(C)cn2c1C(=O)c1ccc(Cl)cc1] | Dimethyl 3-(4-chlorobenzoyl)-6,8-dimethylindolizine-1,2-dicarboxylate | 5610 ± 1085 | 6883 ± 705 | >30000 | 924 ± 127 | 4214 ± 521 |
| KNV11 | 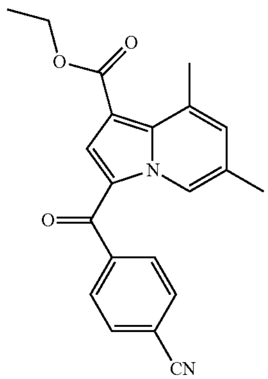 [SMILES: CCOC(=O)c1cc(C(=O)c2ccc(C#N)cc2)n2cc(C)cc(C)c12] | Ethyl 3-(4-cyanobenzoyl)-6,8-dimethylindolizine-1-carboxylate | >30000 | >30000 | >30000 | 8538 ± 1503 | 25854 ± 4203 |
| KNV12 | 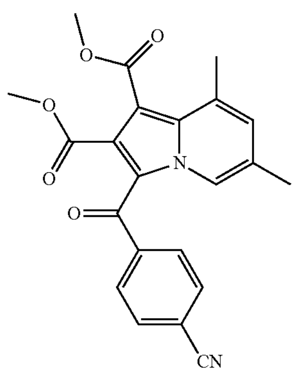 | Dimethyl 3-(4-cyanobenzoyl)-6,8-dimethylindolizine-1,2-dicarboxylate | >30000 | >30000 | >30000 | 12085 ± 1695 | 41142 ± 9215 |
| KNV13 | 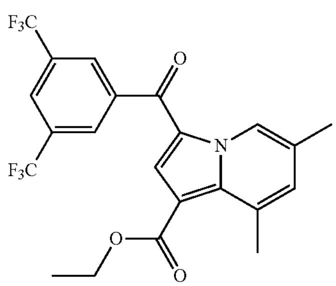 [SMILES: CCOC(=O)c1cc(C(=O)c2cc(C(F)(F)F)cc(C(F)(F)F)c2)n2cc(C)cc(C)c12] | Ethyl 3-(3,5-bis(trifluoromethyl)benzoyl)-6,8-dimethylindolizine-1-carboxylate | >30000 | >30000 | >30000 | 7144 ± 130 | 27954 ± 5215 |

[a]Displacement of specific [$^3$H]-CCPA binding at human A$_1$R expressed in CHO cells.
[b]Displacement of specific [$^3$H]-NECA binding at human A$_{2A}$R expressed in CHO cells.
[c]IC$_{50}$ values obtained inhibiting NECA-stimulated adenylyl cyclase activity in CHO cells expressing hA$_{2B}$R.
[d]Displacement of specific [$^3$H]-HEMADO binding at human A$_3$R expressed in CHO cells.
[e]IC$_{50}$ values obtained counteracting NECA-induced decrease of cAMP accumulation in CHO cells expressing hA$_3$R.
Data are expressed as means ± SE.

All compounds tested showed good affinity and selectivity versus A$_3$AR and antagonistic behavior, which was calculated by the GloSensor™ cAMP assay. The best compound of the series is KNV5 with a high selectivity towards A$_3$AR (K$_i$=213, it is not active in the other subtypes) and with a good antagonistic activity on this receptor (IC$_{50}$=196) demonstrating that this compound is a useful drug on many pathologies in which the A$_3$AR is involved

Example 4

Safety Studies (In Vitro)

The safety of the tested indolizines was evaluated by MTT assay. The MTT (3-(4,5-dimethylthiazol-2-yl)-2,5-diphenyltetrazolium bromide) cytotoxicity assay was used to evaluate the cytotoxic effect of the most promising compounds against peripheral blood mononuclear cells (PBMCs) according to the described protocol. Cells were pipetted (90 mL of cell culture, $1 \times 10^5$ cells/mL) into each well of 96-well microtiter plates, and the outer wells were filled with PBS (phosphate buffer saline) in order to prevent the medium from evaporation during incubation. Thereafter, plates were incubated at 37° C. for 24 h. Each well of the plate was then treated with 10 mL of the compounds (1000-5 µg/mL). In the control wells, the negative control DMSO (dimethyl sulfoxide) and media were added. Thereafter, the plates were incubated for 2 days at 37° C. in a humidified incubator that contained a 5% $CO_2$ atmosphere. After the incubation time, 20 mL of MTT reagent (5 µg/mL) was further added to the individual well. The plate was then incubated for a further 4 h at 37° C. (5% $CO_2$ incubator). The media was then removed, and an aliquot of 100 mL DMSO was added to each well in order to dissolve the formazan crystals that were formed in metabolically active cells. After that, plates were incubated for an extra hour. The absorbance of the formazan was evaluated at 590 nm using an ELISA plate reader (Thermo Scientific Multiskan GO).

It is to be understood that the methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting adenosine receptor activity in a patient, comprising administering to a patient in need thereof a therapeutically effective amount a compound having the formula I:

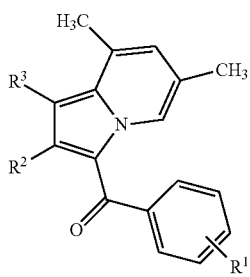

wherein:
$R^1$ is selected from the group consisting of 4-Cl, 4-F, 2-$NO_2$, 3,5-$CF_3$, CN, and $CH_3$;
$R^2$ is $COOCH_3$ or $COOC_2H_5$; and
$R^3$ is H or $COOCH_3$;
wherein the inhibiting the adenosine receptor activity in the patient results in the treatment of one or more pathological conditions of the central and peripheral nervous systems selected from the group consisting of allergies, inflammation, glaucoma, and any combination thereof.

2. A method of treating one or more pathological conditions of the central and peripheral nervous systems selected from the group consisting of allergies, inflammation and glaucoma in a patient, comprising administering to a patient in need thereof a therapeutically effective amount a compound having the formula I:

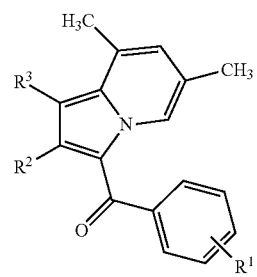

wherein:
$R^1$ is selected from the group consisting of 4-Cl, 4-F, 2-$NO_2$, 3,5-$CF_3$, CN, and $CH_3$;
$R^2$ is $COOCH_3$ or $COOC_2H_5$; and
$R^3$ is H or $COOCH_3$.

3. The method of claim 2, wherein the compound is selected from the group consisting of:
Ethyl 3-(4-chlorobenzoyl)-6,8-dimethylindolizine-1-carboxylate (KNV1);
Ethyl 3-(4-fluorobenzoyl)-6, 8-dimethylindolizine-1-carboxylate (KNV5);
Ethyl 6,8-dimethyl-3-(2-nitrobenzoyl)indolizine-1-carboxylate (KNV6);
Ethyl 6,8-dimethyl-3-(4-methylbenzoyl)indolizine-1-carboxylate (KNV7);
Ethyl 3-(4-cyanobenzoyl)-6,8-dimethylindolizine-1-carboxylate (KNV11);
Dimethyl 3-(4-cyanobenzoyl)-6,8-dimethylindolizine-1,2-dicarboxylate (KNV12); and
Ethyl 3-(3,5-bis(trifluoromethyl)benzoyl)-6,8-dimethyl-indolizine-1-carboxylate (KNV13).

4. A method of claim 1 wherein the compound is selected from the group consisting of:
Ethyl 3-(4-chlorobenzoyl)-6,8-dimethylindolizine-1-carboxylate (KNV1);
Ethyl 3-(4-fluorobenzoyl)-6,8-dimethylindolizine-1-carboxylate (KNV5);
Ethyl 6,8-dimethyl-3-(2-nitrobenzoyl)indolizine-1-carboxylate (KNV6);
Ethyl 6,8-dimethyl-3-(4-methylbenzoyl)indolizine-1-carboxylate (KNV7);
Ethyl 3-(4-cyanobenzoyl)-6,8-dimethylindolizine-1-carboxylate (KNV11);
Dimethyl 3-(4-cyanobenzoyl)-6,8-dimethylindolizine-1,2-dicarboxylate (KNV12); and
Ethyl 3-(3,5-bis(trifluoromethyl)benzoyl)-6,8-dimethyl-indolizine-1-carboxylate (KNV13).

5. The method of claim 4, wherein the adenosine receptor is selected from the group consisting of $hA_1AR$, $hA_2AR$, $hA_3AR$, and a combination thereof.

6. The method of claim 5, wherein the adenosine receptor is $hA_3AR$.

7. The method of claim 5, wherein the adenosine receptor $hA_2AR$ has a subtype selected from the group consisting of $hA_{2A}AR$, $hA_{2B}AR$, and a combination thereof.

\* \* \* \* \*